United States Patent [19]

Rivetti et al.

[11] Patent Number: 5,685,957

[45] Date of Patent: Nov. 11, 1997

[54] METHOD FOR REMOVING ACIDIC AND SALT IMPURITIES FROM AN AQUEOUS CONDENSED PHASE CONTAINING DIMETHYLCARBONATE

[75] Inventors: Franco Rivetti, Milan; Daniele Delledonne, Oleggio, both of Italy

[73] Assignee: Enichem Synthesis S.p.A., Palermo, Italy

[21] Appl. No.: 455,697

[22] Filed: May 31, 1995

[30] Foreign Application Priority Data

Jun. 3, 1994 [IT] Italy .................. MI94A1160

[51] Int. Cl.⁶ .................. B01D 3/00; C07C 68/08
[52] U.S. Cl. .................. 203/41; 159/47.1; 159/DIG. 10; 230/77; 230/80; 230/81; 230/DIG. 25; 210/664; 558/277
[58] Field of Search .................. 203/29, 41, DIG. 25, 203/74, 77, 80, 81, DIG. 23, 38, DIG. 6; 159/47.1, DIG. 10, DIG. 19; 558/277; 210/664, 774, 500.1; 423/419.1, 488

[56] References Cited

U.S. PATENT DOCUMENTS

| | | | |
|---|---|---|---|
| 4,625,044 | 11/1986 | Curnutt | 558/277 |
| 5,344,954 | 9/1994 | Schön et al. | 203/38 |
| 5,359,118 | 10/1994 | Wagner et al. | 203/DIG. 6 |
| 5,440,066 | 8/1995 | Buysch et al. | 203/DIG. 6 |

FOREIGN PATENT DOCUMENTS

| | | |
|---|---|---|
| 0460732 | 12/1991 | European Pat. Off. . |
| 0521480 | 1/1993 | European Pat. Off. . |
| 205101 | 8/1988 | Japan . |
| 267261 | 3/1990 | Japan . |
| 092906 | 6/1994 | Japan . |
| 9305305 | 6/1993 | Rep. of Korea . |

*Primary Examiner*—Virginia Manoharan
*Attorney, Agent, or Firm*—Oblon, Spivak, McClelland, Maier & Neustadt, P.C.

[57] ABSTRACT

Acidic and salt impurities are removed from a condensed phase obtained from dimethyl carbonate synthesis by obtaining the condensed phase from the effluent of a reactor in which carbon monoxide, oxygen and methanol are reacted to form dimethyl carbonate, the condensed phase containing acid and salt impurities, and partially evaporating the condensed phase in an evaporator thereby preparing an evaporated stream substantially free of impurities and a residual bottom stream.

8 Claims, 3 Drawing Sheets

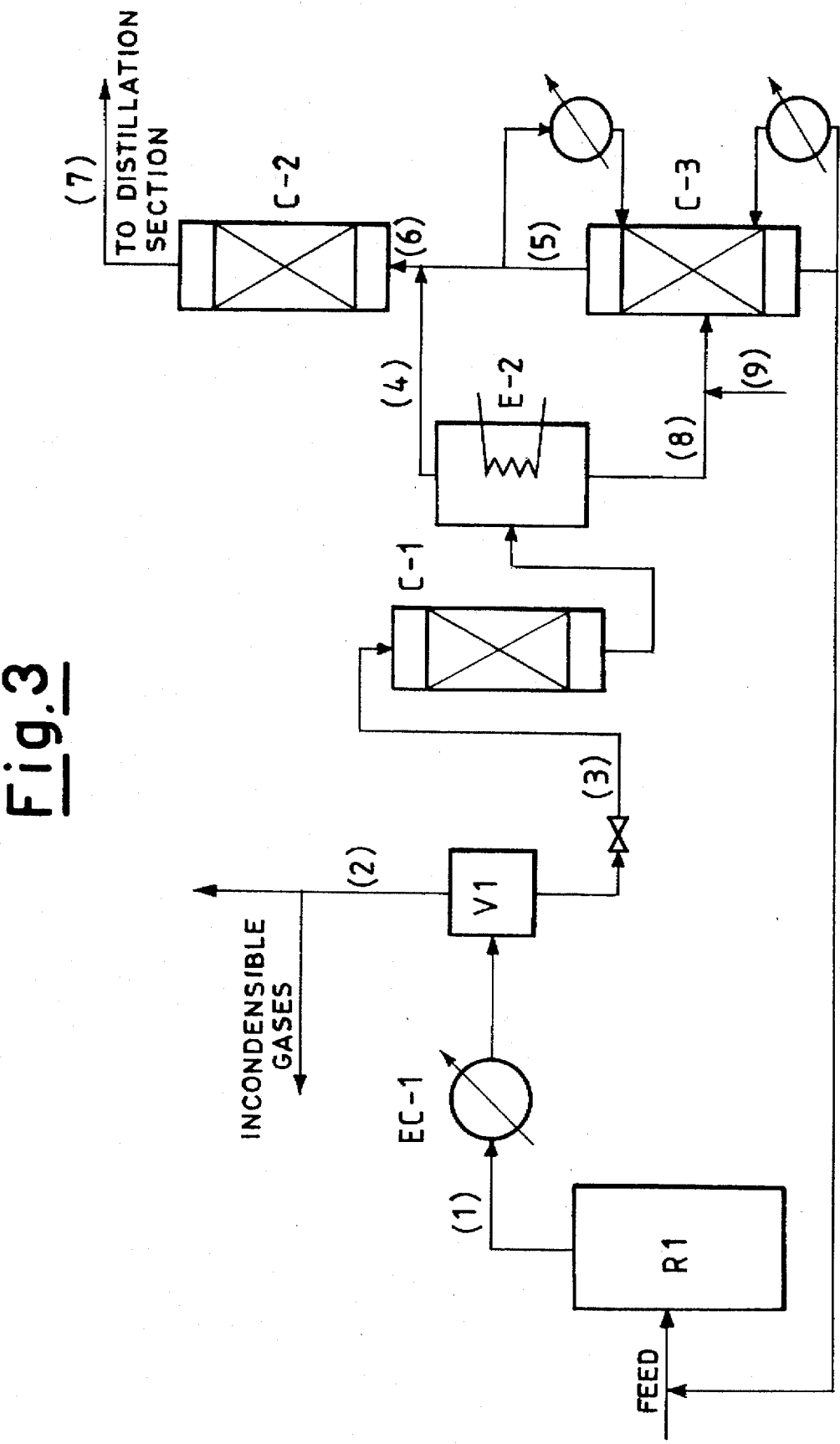

METHOD FOR REMOVING ACIDIC AND SALT IMPURITIES FROM AN AQUEOUS CONDENSED PHASE CONTAINING DIMETHYLCARBONATE

The present invention relates to a method for removing acidic and salt impurities from the condensed phase from the reaction effluent in a process for dimethyl carbonate synthesis.

More particularly, the present invention relates to a method for removing acidic and salt impurities from the condensed phase from the reaction effluent in a process for dimethyl carbonate synthesis, which removal method consists in submitting said phase to partial evaporation.

Dimethyl carbonate ("DMC" herein in the following) is a widely used, very flexible chemical product which is used as such as solvent, or as a fuel additive; furthermore, DMC is an important intermediate product in the synthesis of other alkyl or aryl carbonates useful as synthetic lubricants, solvents, monomers for polymeric materials and for preparing isocyanates, urethanes, ureas and polycarbonates.

At present, the most widely used route for producing DMC is oxidative methanol carbonylation, in particular in the presence of CuCl as a catalyst, according to the reaction equation:

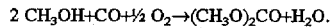

$$2\ CH_3OH + CO + \tfrac{1}{2}\ O_2 \rightarrow (CH_3O)_2CO + H_2O.$$

The preparation of DMC according to such a reaction is disclosed, e.g., in commonly owned U.S. Pat. Nos. 4,218,391 and 4,318,862.

Improvements in the processes claimed in the above U.S. patents are disclosed in commonly owned European patent applications EP-A-460,732 and EP-A-460,735, the contents of which are incorporated thereto by reference, in their entirety, In the above cited patent applications, a continuous process is disclosed for DMC synthesis, according to which the reaction products are removed from the reactor in vapour phase. In such a process, a gas stream exiting the reactor is obtained which contains vapors of water/methanol/DMC system, besides unreacted CO and $O_2$, $CO_2$ which derives from a side reaction, and possible inert gases contained in the feed stream sent to the reactor ($H_2$, Ar, $N_2$, and so forth). This gas/vapor mixture is caused to flow through a condenser which separates a liquid water/methanol/DMC mixture (condensed phase) from noncondensible gases which are mostly recycled to the reaction. The liquid stream of water/methanol/DMC is then fed to the separation unit which allows produced DMC and water to be recovered and unreacted methanol to be recycled to the synthesis.

Unfortunately, such a process is affected by the drawback that the effluent stream of gases and vapours leaving the reactor is contaminated by small amounts of hydrogen chloride, generally comprised within the range of from 30 to 300 ppm by volume (typically corresponding to 100–600 ppm based on condensed phase), which are released from the catalyst used in the reaction. Besides hydrogen chloride, the gas/vapour stream leaving the reactor may possibly contain small amounts of halogen containing copper salts deriving from catalyst entrained by said stream as particulate matter and/or droplets of micron size; the copper amounts entrained in this way are generally comprised within the range of from 1 to 20 Cu mg/Nm³ (corresponding to 1–30 Cu mg/l of condensed phase).

The presence of chloride ions and possible copper ions causes considerable problems of technical-financial character in that facility portion which is downstream of the reactor, in which the operations of product separation and purification are carried out.

In fact, the presence of hydrogen chloride and copper causes very serious problems of equipment corrosion, with the need arising for having resort to special, corrosion resistant materials for building the separation and purification sections, with a considerable increase in equipment costs.

Condensing the vapors contained in the gas stream leaving the synthesis reactor makes it possible a condensed phase containing total hydrogen chloride and copper salts, on the one side, and an noncondensible stream free from such impurities, on the other side, to be obtained, wherein the latter, i.e., the noncondensible stream, can be largely recycled to DMC synthesis section.

The simultaneous removal of chloride and copper ions contained in the condensed phase can be accomplished according to a conventional technique of condensate neutralization by treatment with an alkaline agent. However, in this case, a number of problems arise from precipitation of formed salts, which foul the facility equipment; their separation from process fluids and end disposal of them; and, should an excess of alkaline agent be fed to the reactor, decomposition of produced DMC induced by alkaline hydrolysis.

The removal of the ionic impurities contained in the condensed phase can optionally be carried out by using ion exchange resins. This method is known and widely applied at the industrial level as, e.g., described in Kirk-Othmer, "Encyclopedia of Chemical Technology", III Ed., Vol. 13, page 678. However, one should take into consideration the rather severe limits to the temperature of use of resins. Furthermore, the adsorbing capability of ionic exchange resins is generally rather low, by being comprised within the range of from 4 to 5 equivalents per kg of dry resin. On this bases, while one could think of using cationic exchange resins for removing traces of copper salts contained in the condensed phase, thanks to the extremely low concentrations envisaged for such salts, the use of resins of basic type for removing hydrogen chloride under those conditions would certainly cause problems, owing to the relatively high concentration reached by this impurity in the condensed phase. Furthermore, the use of such resins at an industrial level would be extremely burdensome and difficult, in particular for large capacity facilities, owing to the large resin amounts required, the necessary regeneration frequency and the disposal of the alkaline fluids used in excess in the regeneration.

The present Applicant has now found a method which makes it possible to remove hydrogen chloride and copper salts from the above said condensed phase in an easy and advantageous way, with the level of said impurities being reduced down to such values as to allow equipment made from traditional materials to be used in the sections of DMC separation and purification downstream of synthesis DMC production facilities, thus avoiding all problems associated with the use of traditional neutralization techniques.

Therefore, the object of the present invention is a method for removing acidic and salt impurities from the condensed phase from the reaction effluent in a process for dimethyl carbonate synthesis, which method consists in submitting said phase to partial evaporation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 shows the process scheme embodiment described in Example 3.

Figure 1:
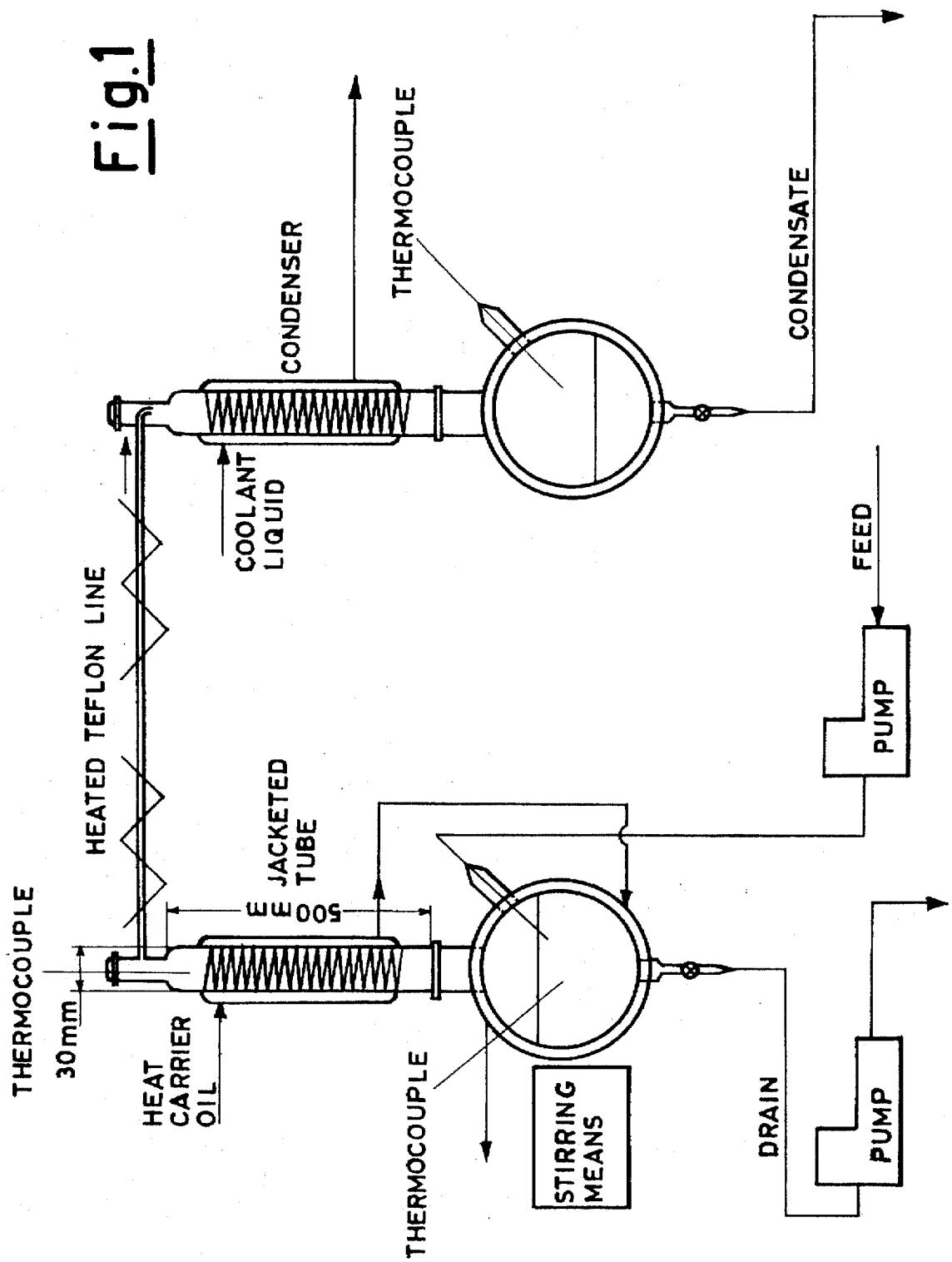
FIG. 1 shows the apparatus arrangement employed to achieve partial evaporation of the condensed phase in Example 1.

From said partial evaporation, an evaporated main stream is obtained which is substantially free from said impurities, together with a secondary, liquid stream, which contains them.

The reaction effluent stream, constituted by a mixture of gases and vapors leaving the reactor for DMC production, is sent to a condenser for recovering, to a practically total extent, the organic component and water contained in the gas/vapour mixture. In this operation, the acidic and salt impurities are separated together with the condensed phase. The noncondensible gases, after condensate separation, which are free from impurities and essentially free from organic vapors and water, are recycled to the reaction section, after preliminary possible purge of inerts and byproducts in gas form ($CO_2$).

The so obtained condensed phase from the reaction effluent is fed to an evaporator which evaporates most of it, generally from 80% to 99%, preferably from 90% to 97%.

During evaporation, hydrogen chloride and possibly present copper are concentrated in the liquid residue and only a small residual fraction, generally comprised within the range of from <1 to 10 ppm by weight, remains in the evaporated stream.

Optionally, the condensed phase, according to an embodiment of the present invention, before being sent to the evaporator, can be treated with an acidic ion exchange resin, advantageously a macroporous polystyrene resin functionalized with sulfonic functions. A residual copper level will be achieved of $\leq 0.1$ mg/l.

According to an embodiment of the invention, the evaporated stream, leaving the evaporator, before being sent to the distillation section, is brought into contact, in vapor phase, with a fixed bed of alumina or modified alumina, or activated charcoal, which completely removes (<1 ppm by weight) residual hydrogen chloride.

According to another embodiment of the present invention, the evaporated stream leaving the evaporator, before being sent to the distillation section, is condensed and brought into contact with a macroporous basic polystyrene resin functionalized with aminic or quaternary ammonium functions, for the complete removal of residual hydrogen chloride (<1 ppm by weight).

The evaporator bottom residue can be recycled to the synthesis section or, according to an embodiment of the invention, before being sent to the synthesis section it can be sent to an exhaustion tower for recovering the organic components and for concentrating the residual aqueous solution of hydrogen chloride (i.e., hydrochloric acid).

The reaction effluent, constituted by a mixture of gases and vapors leaving the reactor for DMC production, is at a pressure which is normally comprised within the range of from 15 to 40 absolute bars, and under a temperature which is normally comprised within the range of from 100° C. to 150° C.

Advantageously, the condensation is carried out under same pressure conditions, by cooling the process fluid down to a temperature which makes it possible the organic components and water to undergo complete condensation, i.e., normally lower than, or equal to, 60° C. In that way, under typical process conditions, approximately 0.4–0.8 kg of condensate per $Nm^3$ of effluent (gases plus vapors) stream from synthesis reactor is obtained, which has the following composition:

methanol: 45%–70% by weight;
dimethyl carbonate: 25%–50% by weight;
water: 2%–6% by weight;

and containing approximately 100–600 ppm by weight of hydrogen chloride and approximately 1–30 ppm by weight of copper.

For the purposes of the present invention, the above disclosed condensate is submitted to partial evaporation. The evaporation is advantageously carried out under atmospheric pressure or under a slightly higher-then-atmospheric pressure, e.g., by operating under a pressure comprised within the range of from 1 to 3 abs. bars; under these conditions, the evaporation temperature is comprised within the range of from 65° C. to 100° C.

The evaporated stream obtained from the partial evaporation as disclosed hereinabove, can be possibly sent to flow over a fixed bed of alumina or activated charcoal. Advantageously, such a passage is carried out under same conditions of pressure and temperature as of evaporation, or at a slightly higher temperature, to prevent any condensation phenomena on the adsorbent bed, with contact times being comprised within the range of from 0.3 to 30 seconds (calculated under normal conditions), to which values of GHSV (Gas Hourly Space Velocity) correspond which are comprised within the range of from 12,000 to 120 $h^{-1}$, more preferably with contact times comprised within the range of from 0.6 to 7.2 seconds, to which GHSV values correspond which are comprised within the range of from 6000 to 500 $h^{-1}$.

The optional operation of treatment with ion exchange resins to remove copper ions from the condensed phase as disclosed above, is advantageously carried out under evaporator pressure, i.e., 1–3 abs. bars, and at condensate temperature, i.e., $\leq 60°$ C., causing the liquid process stream to flow through a resin bed with contact times of higher than or equal to 0.1 hours, preferably comprised within the range of from 0.2 to 0.5 hours.

For this purpose, the cationic ion exchange resins with granular character and macroreticular porous structure (styrene-divinyl benzene sulfonate copolymer) are useful; examples thereof are Amberlyst 15 manufactured by Rohm & Haas or equivalent resins, in their H form. Said resins are capable of retaining, under such conditions as indicated above, copper ion amounts which are of about 1.6 equivalents per liter of wet resin. After the resin material is exhausted, it can be regenerated by treatment with a diluted aqueous solution of hydrochloric acid, e.g., at 5% by weight, causing 1.5–2 $m^3$ of this solution per each $m^3$ of bed to flow through the bed, as well known from the prior art.

The possible treatment of the evaporated stream, coming from the evaporator, with an ion exchange resin for removing residual chloride ions from said stream, as disclosed above, is advantageously carried out, after condensing the vapors under the same pressure as of the evaporator (1–3 abs. bars) and at a temperature close to room temperature ($\leq 60°$ C.), by causing the condensed liquid to flow through a resin bed with contact times longer than, or equal to, 0.1 hours, e.g., comprised within the range of from 0.2 to 0.5 hours.

Useful for that purpose, are, e.g., the strong anionic ion exchange resins with macroreticular porous structure (styrene-divinyl benzene copolymer functionalized with quaternary ammonium functions), in granular form, like Amberlyst A-26, manufactured by Rohm & Haas, or equivalent resins in their basic form. Said resins have the capability of retaining, by operating under such conditions as indicated above, chloride ion amount which are of about 0.8 equivalents per liter of wet resin. After being exhausted, these resins can be regenerated by being treated with a diluted aqueous solution of sodium hydroxide, e.g., at 5% by weight, by causing 1.5–2 $m^3$ of solution per $m^3$ of bed to flow through said bed, as well known from the prior art.

By operating according to the method according to the present invention as disclosed above, the considerable advantage is gained which is due to the fact that the separation/purification facility section downstream of DMC production reactor has fed thereto a process stream which is essentially free from hydrogen chloride and copper ions, thus making it possible said section to be made from normal materials, without any corrosion problems and economic burdens. Differently from the traditional neutralization technique, this outcome is substantially accomplished without using basic neutralizing agents, with the consequent problems of equipment fouling, separation and disposal of the formed salts, and possible dimethyl carbonate decomposition by alkaline hydrolysis being avoided. By contrast, recovered hydrogen chloride and copper can be recycled to synthesis section.

In order to better understand the present invention and to practice it, some illustrative examples are reported in the following, which shall not be construed as being in any way limitative of the purview of the same invention.

EXAMPLE 1

(Partial Evaporation)

The apparatus used in this example is displayed in FIG. 1.

It is essentially constituted by a jacketed flask of 500 ml of capacity, provided with an inlet for liquid feed, a bottom drain and a thermocouple for temperature measurement.

Above the flask a jacketed tube is installed, having a diameter of 30 mm and a height of 500 mm, provided with an inner heated coil and a thermocouple for measuring the temperature of the vapors. A teflon pipe, heated with an electrical heating band, conveys the vapours leaving the head of the evaporator to a condenser kept at 0° C., from which the condensate matter is collected inside a flask.

The evaporator jacketed flask and tube are heated by means of a heat carrier fluid flowing inside the jackets of the apparatuses. Feed to, and drain from, the evaporator flask, are controlled by means of two peristaltic pumps; in this way, one can select the desired evaporation ratio, calculated as percent ratio of:

$$\frac{\text{grams of condensed solution}}{\text{grams of fed solution}} \times 100$$

by operating under constant volume conditions inside the evaporation flask.

The pressure is atmospheric pressure and the evaporation rate is a function of the temperature of the heat carrier fluid.

The concentration of hydrogen chloride is determined by argentometric analysis in feed stream and drain stream to/from evaporation flask; and by colorimetric way, according to as described in UOP Method 317-66T, in the condensate.

By evaporating 125 g/h of a feed having the following composition (percent by weight):

$H_2O$: 6.3%;
$CH_3OH$: 58.5%;
DMC: 35.2%; and
HCl: 505 ppm;

with an evaporation ratio of 90%, 112.5 g/h of condensate is obtained, having the following composition (% by weight):

$H_2O$: 4.7%;
$CH_3OH$: 58.9%;
DMC: 36.4%; and
HCl: 5 ppm;

together with 12.5 g/h of drained stream from flask bottom, having the following composition (% by weight):

$H_2O$: 20.7%;
$CH_3OH$: 54.8%;
DMC: 24.4%; and
HCl: 5000 ppm.

EXAMPLE 2

Evaporation Residue Exhaustion

Figure 2:
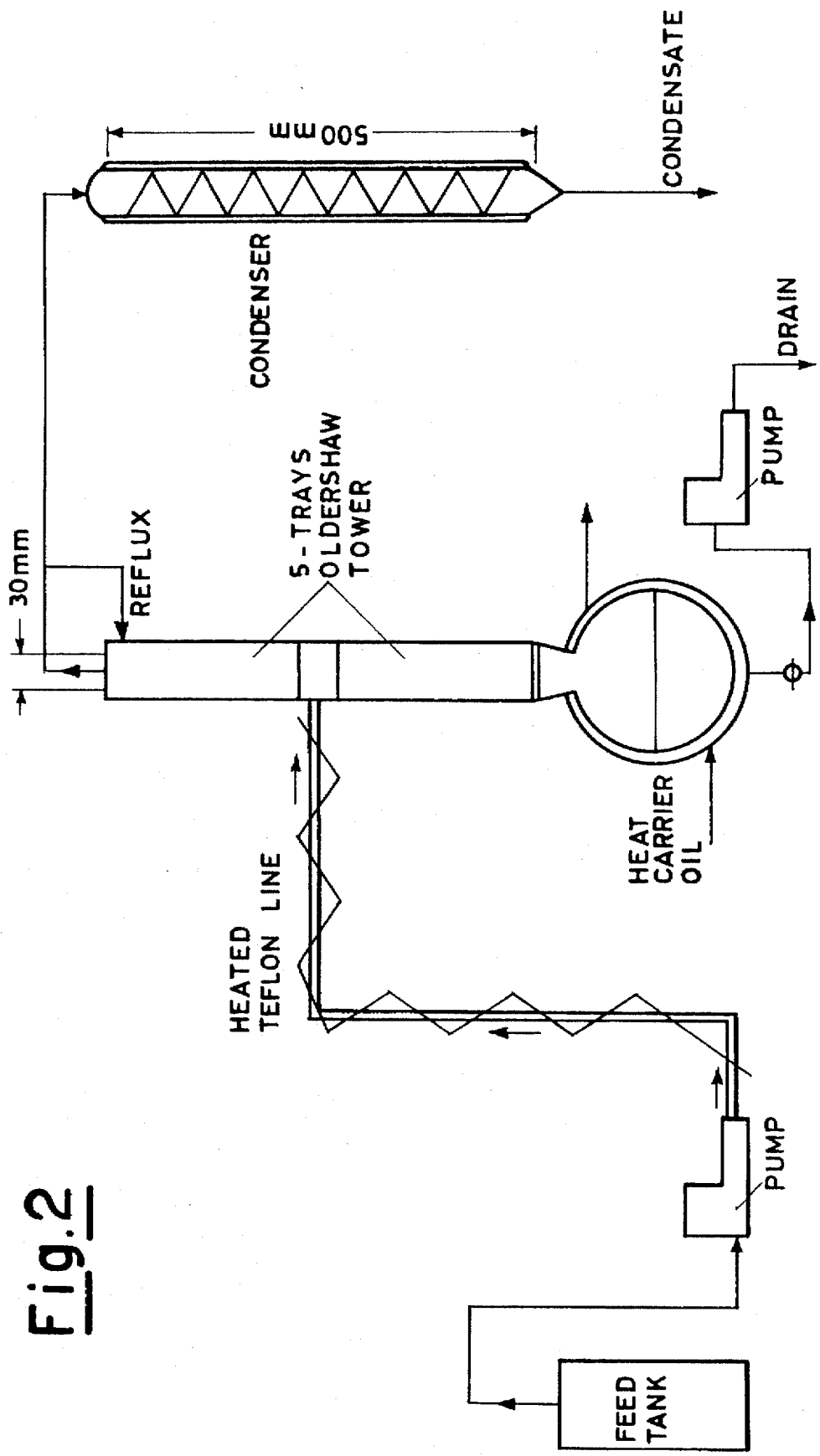
FIG. 2 shows the apparatus arrangement employed for evaporation residue exhaustion as described in Example 2.

The equipment used in this example is displayed in FIG. 2.

It is constituted by two towers of Oldershaw type of 30 mm of diameter, each having 5 trays with 80 holes, mounted above each other and connected through a "T" adapter of glass, which acts as a separator means through which the feed is carried out. The kettle of the tower is constituted by a jacketed flask of 500 ml of capacity, heated with an external-circulation oil thermostat.

The vapor stream leaving the column head is sent to a condenser kept at 0° C. and the resulting condensate streams are weighed and analyzed in order to determine the hydrogen chloride level in them. In a similar way, the drain from the kettle is weighed and analysed in order to detect the hydrogen chloride, organic compounds and water levels.

The liquid feed, before being preheated, is fed to the 5th tray of the bottom Oldershaw tower. The evaporation ratio is fixed by setting the feed flow rate to the tower and the bottom drain flow rate, securing the necessary amount of evaporate by acting on oil bath temperature and keeping constant the level of the liquid phase inside the tower kettle.

The obtained data is reported in Table 1.

TABLE 1

| Feed | Condensate | Evaporation | HCl in head condensate, | HCl in bottom drain, | Bottom drain stream composition, % by weight | | | Reflux | Circulating oil temp. |
|---|---|---|---|---|---|---|---|---|---|
| g/h | g/h | ratio, % | ppm | ppm | $H_2O$ | $CH_3OH$ | DMC | ratio | °C. |
| 150 | 128 | 80 | 1 | 20,380 | 89 | 10.6 | 0.4 | 1:1 | 130 |
| 210 | 192 | 90 | 1 | 37,970 | 100 | 0 | 0 | 1:1 | 140 |
| 370 | 350 | 92 | 1 | 53,470 | 100 | 0 | 0 | 1:1 | 160 |

Feed (% by weight):
$H_2O$: 19.5%
$CH_3OH$: 60.73%
DMC: 19.8%
HCl: 4,105 ppm

EXAMPLE 3

In the description of this example, reference is made to accompanying FIG. 3; in this figure, the numerals in brackets indicate gas or liquid streams.

Inside a reactor (R1) for dimethyl carbonate synthesis operating at the temperature of 130° C. and under the pressure of 24 bars, $CH_3OH$, CO and $O_2$ are continuously reacted in the presence of cuprous chloride as catalyst.

The stream (1) of gases and vapours leaving the reactor has the following composition (% by weight):

$CH_3OH$: 25.7%,

DMC: 7.4%;

$H_2O$: 4.4%;

Other organic species: 1.1%;

$O_2$: 0.2%;

Incondensible inerts: 3.5%;

CO: 49.9%;

$CO_2$: 7.8%

HCl: 145 ppm; and

Cu: 5 mg/$Nm^3$.

The stream (1), 1240 $Nm^3$/h, is sent to heat exchanger (EC-1). The condensate, at 40° C. and 24 bars, which is collected inside tank (V1) has the following composition (% by weight):

$CH_3OH$: 50.8%,

DMC: 41.4%;

$H_2O$: 5%;

Other organic species: 2.8%;

HCl: 330 ppm; and

Cu: 7 ppm.

From (V1) head, overhead stream (2), 785 $Nm^3$/h of incondensible gases is discharged under high pressure, and is recycled to the reaction section, after preliminarily purging accumulated inerts and $CO_2$. The stream (2) has the following composition (% by volume):

CO: 80.0%;

$CO_2$: 12.0%;

Incondensible inerts: 5.6%;

$O_2$: 0.3%;

Other organic species: 0.9%; and $CH_3OH$: 1.1%.

The condensate collected in (V1), after pressure reduction down to 0.4 bar, is fed, together with stream (3), flowing with the flow rate of 870 kg/h, to evaporator (E-2) through the cationic exchange resin bed (C-1) (200 liters of wet resin) for copper removal, the level of which is reduced down to <0.1 ppm.

Evaporator (E-2) operates under a pressure of 1.3 barg and at a temperature of 90° C., evaporating 90% of feed. The vapour stream (4) is thus obtained with the flow rate of 780 kg/h (410 $Nm^3$/h) and the following composition (% by weight):

$CH_3OH$: 67.9%,

DMC: 19.2%;

$H_2O$: 11.0%;

Other organic species: 1.8%; and

HCl: 5 ppm.

This stream is combined with the vapour stream (5) coming from stripper (C-3) head, with the flow rate of 86 kg/h (45 $Nm^3$/h) and the following composition (% by weight):

$CH_3OH$: 60.7%,

DMC: 22.2%;

$H_2O$: 16.7%;

Other organic species: 0.4%; and

HCl: 1 ppm.

The resulting stream (6) flows with the flow rate of 455 $Nm^3$/h and has the following composition (% by weight):

$CH_3OH$: 67.2%,

DMC: 19.5%;

$H^2O$: 11.5%;

Other organic species: 1.7%; and

HCl: 4.5 ppm.

Said resulting stream (6) is caused to flow through the alumina bed (C-2) (alumina volume 200 l). The effluent stream (7) has the same composition, but with a hydrogen chloride level of <1 ppm and is directly fed in vapor phase, to the distillation section, for recovering the produced DMC.

From evaporator (E-2) a liquid bottom stream (8) is recovered with a flow rate of 87 kg/h and the following composition (% by weight):

$CH_3OH$: 45.0%,

DMC: 46.2%;

$H_2O$: 7.8%;

Other organic species: 0.7%; and

HCl: 3300 ppm.

Such a stream, admixed with water [stream (9), having a flow rate of 2 kg/h] is sent to stripper (C-3) for recovery of organic species, Column (C-3) operates under a pressure of 1.7 bar. The overhead distilled stream, stream (5) is combined in vapour phase with the evaporator head stream (4) and the resulting combined stream is sent to (C-2). The bottom product is constituted by an aqueous solution of hydrogen chloride (hydrochloric acid) at 10% by weight (3 kg/h), which is recycled to the synthesis reactor.

We claim:

1. A method of removing hydrochloric acid and salt impurities from a process of synthesizing dimethyl carbonate comprising:

obtaining a condensed phase from an effluent of a reactor in which carbon monoxide, oxygen and methanol are reacted to form dimethyl carbonate, said condensed phase containing hydrochloric acid and salt impurities;

partially evaporating said condensed phase in an evaporator thereby producing an evaporated stream substantially free of hydrochloric acid and salt impurities and a bottom drain stream containing most of the hydrochloric acid and salt impurities, said evaporated stream constituting from 80 to 99% by wt. of the condensed phase passed into said evaporator; and distilling said evaporated stream in a distillation unit to obtain a purified dimethyl carbonate.

2. The method of claim 1, which further comprises passing said evaporated stream in vapor phase through a fixed bed of alumina, modified alumina or activated charcoal prior to passing the evaporated stream into said distillation unit.

3. The method of claim 1, which further comprises condensing said evaporated stream and contacting the condensed evaporated stream with a basic, microporous polystyrene resin functionalized with aminic or quaternary ammonium functional groups prior to passing the condensed evaporated stream into said distillation unit.

4. The method of claim 1, wherein the bottom drain stream is recycled to said reactor.

5. The method of claim 1, wherein the bottom drain stream is passed to an exhaustion tower to recover organic components from the evaporated stream thereby forming a residual aqueous material containing hydrochloric acid which is returned to the reactor.

6. The method of claim 1, wherein said amount of condensed phase evaporated is 90 to 97% by weight.

7. The method of claim 1, wherein the partial evaporation is conducted in an evaporator under an absolute pressure of 1 to 3 bars and at a temperature ranging from 65° to 100° C.

8. The method of claim 1, which further comprises, prior to passing said condensed phase to said evaporator, treating said condensed phase with an acidic ion exchange resin.

* * * * *